US007544370B2

(12) United States Patent
Venkata Ramana Rao et al.

(10) Patent No.: US 7,544,370 B2
(45) Date of Patent: Jun. 9, 2009

(54) PANTOPRAZOLE MULTIPARTICULATE FORMULATIONS

(75) Inventors: Sripriya Venkata Ramana Rao, Iselin, NJ (US); Syed M. Shah, East Hanover, NJ (US); Hanumantharao Tatapudy, Suffern, NJ (US); Richard William Saunders, Palisades, NY (US); Mahdi Fawzi, Morristown, NJ (US); Arwinder Nagi, Thiells, NY (US); Shailesh Singh, Bardonia, NY (US); Sumon A. Hasan, Monroe, NY (US)

(73) Assignee: Wyeth, Madison, NJ (US)

( * ) Notice: Subject to any disclaimer, the term of this patent is extended or adjusted under 35 U.S.C. 154(b) by 495 days.

(21) Appl. No.: 10/955,567

(22) Filed: Sep. 30, 2004

(65) Prior Publication Data

US 2005/0129761 A1    Jun. 16, 2005

Related U.S. Application Data

(60) Provisional application No. 60/507,810, filed on Oct. 1, 2003.

(51) Int. Cl.
*A61K 9/64* (2006.01)
(52) U.S. Cl. .................................... 424/456
(58) Field of Classification Search ........... None
See application file for complete search history.

(56) References Cited

U.S. PATENT DOCUMENTS

| | | | |
|---|---|---|---|
| 3,065,143 A | 11/1962 | Christenson et al. | |
| 4,255,431 A | 3/1981 | Junggren et al. | |
| 4,686,230 A | 8/1987 | Rainer et al. | |
| 4,758,579 A | 7/1988 | Kohl et al. | |
| 4,853,230 A | 8/1989 | Lovgren et al. | |
| 5,178,867 A | 1/1993 | Guittard et al. | |
| 5,225,202 A | 7/1993 | Hodges et al. | |
| 5,260,069 A | 11/1993 | Chen | |
| 5,273,758 A | 12/1993 | Royce | |
| 5,433,959 A | 7/1995 | Makino et al. | |
| 5,731,002 A | 3/1998 | Olovson et al. | |
| 5,753,265 A * | 5/1998 | Bergstrand et al. | 424/474 |
| 5,780,057 A | 7/1998 | Conte et al. | |
| 5,811,426 A | 9/1998 | Heeres et al. | |
| 5,888,535 A | 3/1999 | Gray | |
| 5,945,124 A | 8/1999 | Sachs et al. | |
| 5,997,903 A | 12/1999 | Dietrich et al. | |
| 6,013,281 A | 1/2000 | Lundberg et al. | |
| 6,068,856 A | 5/2000 | Sach et al. | |
| 6,077,541 A | 6/2000 | Chen et al. | |
| 6,093,734 A | 7/2000 | Garst et al. | |
| 6,096,340 A | 8/2000 | Chen et al. | |
| 6,132,768 A | 10/2000 | Sachs et al. | |
| 6,132,771 A | 10/2000 | Depui et al. | |
| 6,136,344 A | 10/2000 | Depui et al. | |
| 6,159,499 A * | 12/2000 | Seth | 424/451 |
| 6,248,363 B1 | 6/2001 | Patel et al. | |
| 6,274,173 B1 | 8/2001 | Sach et al. | |
| 6,277,412 B1 | 8/2001 | Otterbeck | |
| 6,296,876 B1 | 10/2001 | Odidi et al. | |
| 6,328,993 B1 | 12/2001 | Linder et al. | |
| 6,346,269 B1 | 2/2002 | Hsiao et al. | |
| 6,365,184 B1 | 4/2002 | Depui et al. | |
| 6,379,705 B1 | 4/2002 | Mendes et al. | |
| 6,383,510 B1 | 5/2002 | Linder et al. | |
| 6,391,342 B1 | 5/2002 | Henriksen et al. | |
| 6,479,075 B1 | 11/2002 | Odidi et al. | |
| 6,489,346 B1 | 12/2002 | Phillips | |
| 6,531,152 B1 | 3/2003 | Lerner et al. | |
| 6,551,620 B2 | 4/2003 | Otterbeck | |
| 6,559,167 B1 | 5/2003 | Garst et al. | |
| 6,569,453 B2 | 5/2003 | Linder et al. | |
| 6,569,463 B2 | 5/2003 | Patel et al. | |
| 6,602,522 B1 | 8/2003 | Chen et al. | |
| 6,605,303 B1 | 8/2003 | Karehill et al. | |
| 6,607,742 B2 | 8/2003 | Linder et al. | |
| 6,610,323 B1 | 8/2003 | Lundberg et al. | |
| 6,617,338 B2 | 9/2003 | Mali et al. | |
| 6,623,759 B2 | 9/2003 | Hesse et al. | |

(Continued)

FOREIGN PATENT DOCUMENTS

AU   2005204242 A2   9/2005

(Continued)

OTHER PUBLICATIONS

I.C. Rodríguez, *Sistemas de liberación Bioadhesivos (Bioadhesive Release Systems, Bioadhesive delivery systems)*, Ars Pharmaceutica, 41(1):115-128, 2000.

(Continued)

*Primary Examiner*—M P Woodward
*Assistant Examiner*—Bethany Barham
(74) *Attorney, Agent, or Firm*—Paul Carango, Esq.; Howson & Howson LLP

(57) ABSTRACT

Pantoprazole sodium multiparticulates are described which avoid sticking to nasogastric and gastronomy tubes. The pantoprazole multiparticulates have a spheroid core of pantoprazole or an enantiomer thereof, or a salt thereof, a surfactant, and a disintegrant; a sub coat which is comprised of hydroxypropyl methylcellulose (hypromellose) and water, an enteric coat on the sub-coat, and a final seal coat over the enteric coat, which is composed of hydroxypropyl methylcellulose (hypromellose) and water.

22 Claims, No Drawings

U.S. PATENT DOCUMENTS

| | | |
|---|---|---|
| 6,645,988 B2 | 11/2003 | Phillips |
| 6,699,885 B2 | 3/2004 | Phillips |
| 6,730,685 B1 | 5/2004 | Brulls |
| 6,749,867 B2 | 6/2004 | Robinson et al. |
| 6,780,436 B1 | 8/2004 | Lopez-Cabrera et al. |
| 6,780,882 B2 | 8/2004 | Phillips |
| 6,953,808 B2 | 10/2005 | Gray |
| 7,041,313 B1 | 5/2006 | Dietrich et al. |
| 7,220,762 B1 | 5/2007 | Ukai et al. |
| 2001/0053387 A1 | 12/2001 | Hamied et al. |
| 2002/0012676 A1 | 1/2002 | Lundberg et al. |
| 2002/0039597 A1 | 4/2002 | Ukai et al. |
| 2002/0128293 A1 | 9/2002 | Rampal et al. |
| 2003/0118650 A1 | 6/2003 | Lizcano Garcia et al. |
| 2004/0028737 A1 | 2/2004 | Deshpande et al. |
| 2004/0146558 A1 | 7/2004 | Hirata et al. |
| 2004/0219211 A1 | 11/2004 | Criere et al. |
| 2005/0003005 A1 | 1/2005 | Shimizu et al. |
| 2005/0042277 A1 | 2/2005 | Srinivas et al. |
| 2005/0042285 A1 | 2/2005 | Ukai et al. |
| 2005/0220870 A1 | 10/2005 | Hepburn et al. |
| 2005/0239844 A1 | 10/2005 | Lee et al. |
| 2005/0245578 A1 | 11/2005 | Allegrini et al. |
| 2005/0266075 A1 | 12/2005 | Chebil |
| 2006/0057195 A1 | 3/2006 | Nomomura et al. |
| 2006/0165797 A1 | 7/2006 | Plachetka |
| 2006/0189590 A1 | 8/2006 | Kohl et al. |
| 2006/0216346 A1 | 9/2006 | Dietrich et al. |
| 2006/0235053 A1 | 10/2006 | Gebauer et al. |
| 2006/0240100 A1 | 10/2006 | Anstett |
| 2006/0257467 A1 | 11/2006 | Kostadinov et al. |
| 2006/0263426 A1 | 11/2006 | Dietrich et al. |

FOREIGN PATENT DOCUMENTS

| | | |
|---|---|---|
| DE | 42 19 390 A1 | 12/1992 |
| DE | 197 52 843 A1 | 7/1997 |
| EP | 0 005 129 A1 | 10/1979 |
| EP | 0 124 495 A2 | 11/1984 |
| EP | 0 166 287 A1 | 1/1986 |
| EP | 0 174 726 A1 | 3/1986 |
| EP | 0 244 380 A2 | 11/1987 |
| EP | 0 249 587 B1 | 12/1987 |
| EP | 0 268 956 B2 | 6/1988 |
| EP | 0 434 999 A1 | 7/1991 |
| EP | 0 514 008 B1 | 11/1992 |
| EP | 0 519 365 A1 | 12/1992 |
| EP | 0 526 862 B1 | 2/1993 |
| EP | 0 793 959 A1 | 9/1997 |
| EP | 1 108 425 B1 | 6/2005 |
| EP | 1 043 976 B1 | 12/2005 |
| EP | 0 960 620 B1 | 1/2006 |
| EP | 1 652 514 A1 | 5/2006 |
| GB | 2163347 A | 3/1986 |
| WO | WO 92/22284 | 12/1992 |
| WO | WO 94/02140 A1 | 2/1994 |
| WO | WO 94/27988 | 12/1994 |
| WO | WO 96/01623 A1 | 1/1996 |
| WO | WO96/01624 A1 | 1/1996 |
| WO | WO 96/01625 A1 | 1/1996 |
| WO | WO 96/23500 A1 | 8/1996 |
| WO | WO 96/24338 A1 | 8/1996 |
| WO | WO 97/02020 | 1/1997 |
| WO | WO 97/02021 A1 | 1/1997 |
| WO | WO 97/12580 | 4/1997 |
| WO | WO 97/25979 | 7/1997 |
| WO | WO 97/47285 A1 | 12/1997 |
| WO | WO 97/48380 A1 | 12/1997 |
| WO | WO 98/00115 | 1/1998 |
| WO | WO 99/06027 A1 | 2/1999 |
| WO | WO 99/18938 A1 | 4/1999 |
| WO | WO 99/27917 | 6/1999 |
| WO | WO 00/09092 | 2/2000 |
| WO | WO 01/28559 A1 | 4/2001 |
| WO | WO 2004/004682 A2 | 1/2004 |
| WO | WO 2004/004718 A1 | 1/2004 |
| WO | WO 2004/035052 A1 | 4/2004 |
| WO | WO 2004/066982 A1 | 8/2004 |
| WO | WO 2004/080439 A1 | 9/2004 |
| WO | WO 2004/089333 A2 | 10/2004 |
| WO | WO 2004/098573 A1 | 11/2004 |
| WO | WO 2004/098577 A3 | 11/2004 |
| WO | WO 2004/098594 A3 | 11/2004 |
| WO | WO 2005/004921 A1 | 1/2005 |
| WO | WO 2005 001637 A1 | 2/2005 |
| WO | WO 2005/107721 A2 | 11/2005 |

OTHER PUBLICATIONS

Wyeth-Ayerst, Product Information (revised Jul. 10, 2003), Protonix Physician's Desk Reference, 2003, pp. 3461-3464.

M. Summers and M. Aulton, Chapter 25 Granulation in Pharmaceutics: Science of Dosage Form Design by Aulton, Michael E., Second ed. (Churchill Livingstone) p. 364, 365, 374.

Chun et al. "Lansoprazole: An Alternative Method of Administration of a Capsule Dosage Formulation" Clinical Therapeutics, vol. 17, No. 3, (1995) pp. 441-447.

Protonix® Revised Dec. 2007, Product Literature, "For Delayed-Release Oral Suspension", pp. 1-20.

Protonix, Pantoprazole Sodium, Product Literature, Revised Apr. 2008.

* cited by examiner

PANTOPRAZOLE MULTIPARTICULATE FORMULATIONS

CROSS-REFERENCE TO RELATED APPLICATION

This application claims the benefit under 35 USC 119(e) of prior U.S. Provisional Patent Application No. 60/507,810, filed Oct. 1, 2003.

BACKGROUND OF THE INVENTION

Pantoprazole, 5-(difluoromethoxy)-2-[(3,4-dimethoxy-2-pyridyl)methylsulphinyl]-1H-benzimidazole, is a H+/K+-adenosine triphosphate (ATP) inhibitor (also known as acid pump or proton pump inhibitor (PPI), is an enzyme present in the gastric parietal cells. It is believed that these drugs are metabolized in the parietal cells to active sulfenamide metabolites that inactivate the sulfhydryl group of the proton pump, thus reducing the hydrogen ion secretion. PPIs are generally lipophilic weak bases with poor aqueous solubility at low pH. Many PPIs are unstable in low pH solutions and undergo rapid acid-catalyzed degradation, and they are relatively stable at neutral or high pH.

The current commercial oral formulations of sodium pantoprazole are single unit coated tablets. See, e.g., U.S. Pat. No. 5,997,903, which describes oral forms of pantoprazole that consist of a core, an intermediate layer and an outer layer. The current coating has a tendency to cause undesirable sticking of the tablet to the gastrointestinal tract.

Multiparticulate formulations, because of their nature of dispersing in the gastrointestinal tract, show a reduced food effect and variability in gastric emptying times, thereby providing for reduced inter and intra subject variability, as compared to single unit tablets (Intl. Journal of Pharmaceutics 140 [1996] 229-235).

Several unsuccessful attempts have been made in the past to develop a multiparticulate formulation of pantoprazole. However, these attempts yielded multiparticulates that were not bioequivalent to tablets, only 70% relative bioavailability was found. Another attempt using different technologies-non-pareil seed coating and extrusion/spheronization, resulted in a product that did not provide the appropriate release in acid conditions. In addition, these attempts yielded product that was unstable, as observed by discoloration, when stored at room temperature.

SUMMARY OF THE INVENTION

The invention provides a stable multiparticulate pantoprazole formulation that provides reduced inter and intra subject variability.

In one embodiment, the pantoprazole multiparticulates of the invention is composed of a spheroid core comprising pantoprazole or an enantiomer thereof, or a salt or hydrate thereof, at least one surfactant, at least one distinegrant, and about 1% to about 2% w/w water; an enteric coat on the core, said enteric coat comprising a copolymer of methacrylic acid and methacrylates in the range of about 15 to about 45% w/w of the spheroid core; wherein said multiparticulates have an average size of about 1 mm in diameter.

Advantageously, the multiparticulate formulations of the invention are stable under room temperature storage conditions for at least twelve months. Based on the trend analysis using the twelve month room temperature data and 6 month 40° C./75% relative humidity (RH) data available to date, the multiparticulates of the invention should have a shelf life of over 2 years. Typically, a multiparticulate formulation of the invention is considered stable if it retains 90% to 110% of its potency during shelf life storage.

This pantoprazole multiparticulate formulation of the invention is less prone to adherence to the intestinal walls, nasogastric and gastromy tubes, and pouch material thereby giving predictable delivery of the drug product to the site of drug release. It also provides for an early onset of action for relief of gastro-intestinal pain and has a prolonged duration of action. This formulation allows dosing to pediatric patients and patients who have difficulty swallowing solid foods. This formulation also allows for drug delivery via nasogastric and gastrostomy tubes.

DETAILED DESCRIPTION OF THE INVENTION

The present invention provides a multiparticulate formulation of pantoprazole having a unique combination of excipients and a surfactant (e.g., polysorbate 80) that are compatible with pantoprazole sodium in the presence of an alkaline pH environment. Further, the invention provides a process that utilizes low shear during granulation and low temperature during drying for preparation of the multiparticulate. This process contributes to the stability of the core of the multiparticulates of the invention.

In one aspect, the invention provides multiparticulate formulations of pantoprazole having reduced release under gastric conditions and fast release at neutral pH, i.e., in the lower gastrointestinal tract.

The multi particulate formulation of sodium pantoprazole of the invention provides an enhanced system for the delivery of pantoprazole to patients. The current marketed formulation is a single monolithic tablet. The present formulation of multiparticulate spheroids, which is adaptable for use in a capsule or a foil packet, can be prepared by extrusion/spheronization plus coating technology.

The composition of the multiparticle of the invention, and the enteric coat, e.g., Eudragit, allows for reduced release at low pH (~1) and fast release at a neutral pH (~7). This provides faster blood levels of the drug, in patients, and thereby a faster onset of action. The smaller $T_{lag}$ value of multiparticulate formulation as compared to that of a single monolithic tablet based on the results from dog data indicates faster onset of action of multiparticulate formulation.

The use of a multi particulate formulation facilitates dosing to pediatric patients and patients who have trouble swallowing, by dispersing the spheroids in a suspending liquid or sprinkling/dispersing in a low pH liquid like applesauce, prior to administration. The suspending liquid could be made prior to administration by mixing a blend of powder material with water. The smaller size of the multi particulates, in a capsule or pouch or any other container, also allows dosing through nasogastric or gastrostomy tube.

This formulation allows for a faster relief of GI pain, and prolonged duration of action (extended release), as compared to the current marketed tablet.

I. Multiparticulates of the Invention

Suitably, the multiparticles are in the range of about 0.1 to 2 mm, or 0.5 mm to 1.5 mm, or 0.7 mm to 1.25 mm, or 0.8 mm to 1 mm. In one embodiment, the multiparticulates in a composition of the invention average about 1 mm in diameter. Typically, the multiparticles of the invention are no greater than about 1 mm in size in order to facilitate passage through nasogastric tubes.

The multiparticulates of the invention are composed, at a minimum, of a spheroid core with an enteric coat over the core. In between the core and enteric coat an initial seal coat may be applied, e.g., comprising a coating of hydroxylpropyl methylcellulose (hypromellose). Also, over the enteric coat a final seal coat may be applied, e.g., a coating of hydroxylpropyl methyl cellulose (hypromellose). The spheroid core is composed of, at a minimum, a pantoprazole or a salt thereof, and a surfactant.

As used herein unless the context requires otherwise, the term 'pantoprazole' refers to 5-(difluoromethoxy)-2-[(3,4-dimethoxy-2-pyridyl)methylsulphinyl]-1H-benzimidazole and enantiomers thereof and the term 'pantoprazole compound' includes pantoprazole and enantiomers and salts and hydrates thereof. The active compound, pantoprazole is described in European Patent 166 287, which describes the preparation thereof, and is available commercially under the brand name PROTONIX®. Examples of pharmaceutically acceptable salts of pantoprazole include, e.g., sodium, magnesium, and calcium, among others; still others are described in the European Patent 166 286, which is incorporated by reference herein. The selection of a suitable salt is not a limitation of the invention. In one embodiment, the salt is sodium. Typically, the pantoprazole compound is present in the range of from about 5 to 50% w/w, more preferably about 20 to 45% w/w, of the total multiparticulate.

Suitable surfactants are known to those of skill in the art. However, particularly desirable are sodium lauryl sulfate, polysorbates, including, e.g., polysorbate 80, and mixtures of these components. Typically, the surfactant is present in the core in an amount of about 2 to about 7% w/w, and desirably, about 5% w/w of the core. In another embodiment, the surfactant is present in a ratio of about 5:3 drug: surfactant (e.g., pantoprazole sodium sesquihydrate to sodium lauryl sulfate) to about 10:1 drug: surfactant (e.g., pantoprazole sodium sesquihydrate to polysorbate 80). Advantageously, the surfactants in the multiparticulate formulation have been found to enhance the wettability and, thus, the speed and extent of release and absorption of the sodium pantoprazole, from the multi particulate formulation of the invention.

The spheroid core can further contain a disintegrant, a pH adjuster and, optionally a binder or another excipient such as hydroxypropyl methylcellulose (e.g., hypromellose 2208). Suitably, the total amount of disintegrant(s) present in the core is an amount of about 15% w/w to about 80% w/w, or about 20% w/w to about 70% w/w, or about 25% w/w to about 45% w/w, or about 30% w/w to about 42% w/w. In one embodiment, the total amount of drug to binder is represented by a ratio of from about 50:1 to about 40:1 by weight drug: binder. The total amount of a pH adjuster in the formulation can range from about 0.1% w/w to about 10% w/w of the multiparticulate, or about 1% w/w to about 8% w/w, or about 3% w/w to about 7% w/w. However, these percentages can be adjusted as needed or desired by one of skill in the art.

The disintegrant may be selected from among other known disintegrants, including, e.g., cellulose, and crospovidone, among others. In one embodiment, the disintegrant is selected from among microcrystalline cellulose and crospovidone, and mixtures thereof. The binder may be selected from among known binders, including e.g., cellulose, and povidone, among others. In one embodiment, the binder is hydroxylpropyl methyl cellulose (hypromellose). Suitable pH adjusters include, e.g., sodium carbonate, sodium bicarbonate, potassium carbonate, lithium carbonate, among others. Still other suitable components will be readily apparent to one of skill in the art.

In one embodiment, the spheroid core contains, w/w based on the dry uncoated core, about 45% pantoprazole sodium sesquihydrate (about 40% free pantoprazole), about 25 to 30%, and preferably about 27% microcrystalline cellulose, about 4 to 6%, and preferably about 5% polysorbate 80, about 14 to 16%, and preferably about 15% crospovidone, about 0.5 to 2%, and preferably about 1% hypromellose 2208, about 5 to 8%, and preferably about 6.5% sodium carbonate. In one embodiment, the spheroid core contains:

| | |
|---|---|
| pantoprazole sodium sesquihydrate | 45.24% w/w |
| microcrystalline cellulose | 27.25% w/w |
| polysorbate 80 | 5% w/w |
| crospovidone | 15% w/w |
| hypromellose 2208 | 1% w/w |
| sodium carbonate | 6.5% w/w |

In another embodiment, the spheroid core contains:

| Ingredients | Amount/ Capsule | % w/w, based on total weight multiparticulate |
|---|---|---|
| Pantoprazole Sodium Sesquihydrate | 45.11 | 21.911 |
| Microcrystalline Cellulose, NF/EP (Avicel PH 101) | 27.39 | 13.304 |
| Polysorbate 80, NF Vegetable source | 5.00 | 2.429 |
| Crospovidone, NF (Polyplasdone XL) | 15.00 | 7.286 |
| HPMC USP/EP (Methocel) K3 | 1.00 | 0.486 |
| Sodium Carbonate, NF | 6.50 | 3.157 |
| Purified Water, USP/BP/EP | | q.s. to make wet mass* |
| Total | 100.00 mg | 48.573 |

Although moisture is removed from the core during the drying process which is described below, the core preferably retains about 1% to about 2% w/w water. Without wishing to be bound by theory, the inventors believe that this water content contributes the stability of this multiparticulate as compared to the failed prior art attempts at forming a multiparticulate pantoprazole.

Optionally, an initial seal coat (or subcoat) can be applied directly to the core prior to coating with the enteric coat. Although the components of this seal coat can be modified by one of skill in the art, a particularly suitable initial seal coat is composed of hydroxypropyl methylcellulose (hypromellose) and water. For example, a suitable initial seal coat can be applied as a 7.5% w/w hypromellose solution. Typically, such a seal coat is in the range of about 2% w/w to about 4% w/w of the uncoated core or about 1% w/w to about 2% w/w of the coated multiparticulate.

In one embodiment, a multiparticulate with a subcoat contains:

| Ingredients | Amount/ Capsule | % w/w, based on total weight multiparticulate |
|---|---|---|
| A. Sub Coat: | 4.00 mg | 1.943 |
| Pantoprazole Sodium Pellets (40 mg pantoprazole per 100 mg pellets) | 100.00 mg | 48.573 |
| Hydroxypropylmethyl cellulose 2910, USP, 6 cps | 4.00 mg | 1.943 |
| Purified water, USP/BP/EP | 9.33 mg* | |
| Total | 104.00 mg | 50.516 |

*removed during processing

The enteric coat is applied over the initial seal coat, if present, or directly to the uncoated spheroid core. Suitably, the enteric coat is applied such that it coats the core in an amount of about 15 to 45% w/w, or about 20% w/w to about 30% w/w, or about 25% w/w to 30% w/w of the multiparticulate. In one embodiment, the enteric coat is about 27.5 to 32.5% w/w of the multiparticulate. Suitably, the enteric coat contains a product which is a copolymer of methacrylic acid and methacrylates, such as the commercially available Eudragit L 30D-55. In one embodiment, the enteric coat is composed of a Eudragit L 30D-55 copolymer, talc, triethyl citrate, sodium hydroxide and water. More particularly, the enteric coating may contain about 30% w/w of multiparticulate (applied as a 30 wt % dispersion) of Eudragit L 30D-55 coating; about 15% w/w talc, about 3% triethyl citrate; a pH adjuster such as sodium hydroxide and water. Other suitable materials may be selected for use in the enteric coat including, e.g., hydroxypropyl methylcellulose phthalate, cellulose acetate phthalate and the like.

In one embodiment, a multiparticulate of the invention is provided with a subcoat over the core and an enteric coat as follows:

| Ingredients | Amount/capsule | % w/w, based on total weight multiparticulate |
|---|---|---|
| Core + Subcoat | 100.20 mg | 48.67 |
| Eudragit L30D-55 | 208.00 mg<br>62.40 (solids) | 30.309 |
| Talc, USP, Altalc 500 V | 31.20 mg | 15.155 |
| Sodium Hydroxide, NF 1 N solution | 9.30 mg<br>0.36 (solids) | 0.175 |
| Triethyl Citrate, PG/NF | 6.24 mg | 3.031 |
| Purified Water, USP/BP/EP | 183.38 mg* | |
| Total | 204.20 mg | 99.186 |

*removed during processing

In one embodiment, the enteric-coated multiparticulate is further coated with a final seal coat. Suitably, this final seal coat is comprises hydroxypropyl methylcellulose, and about 0.1% w/w to 10% w/w of the coated multiparticle, 0.1% w/w to about 5% w/w, or about 0.2% w/w to about 4% w/w.

In one embodiment, a final seal coat of hydroxypropyl methylcellulose in an amount of 0.5 to 1% w/w of the multiparticulate in water (which is removed during processing) is applied over the enteric coat. Following this, a coating of talc can optionally be applied over the final seal coat, in an amount of about 0.05 w/w to about 1% w/w, and preferably 0.1% w/w to 0.5% w/w.

In one embodiment, the resulting multiparticulate formulation of the invention achieves a geometric mean AUC ratio of test/reference of 89 to 94 with a 90% confidence interval of 84 to 100 for the ratio or achieving a geometric mean Cmax ratio of test/reference of 62 to 66 with a 90% confidence interval of 56 to 74 for the ratio or an in-vitro dissolution profile as shown below:

| Media | Time | | % Drug Release | | Target |
|---|---|---|---|---|---|
| | | Initial | 6 Months @ 25 C./ 60% RH | 6 Months @ 40 C./ 75% RH | |
| Acid (pH 1.0) | 2 hrs | 0.33 | 0.45 | 0.6 | NMT 10% |
| Followed by Alkaline Buffer (pH 6.8) | 3 min | — | 0.91 | 0.85 | — |
| | 6 min | — | 3.61 | 1.83 | — |
| | 9 min | — | 52.25 | 16.45 | — |
| | 12 min | — | 89.65 | 75.15 | — |
| | 15 min | 101.58 | 97.15 | 91.92 | — |
| | 30 min | 105.29 | 100.67 | 98.96 | — |
| | 45 min | 105.29 | 100.57 | 99.14 | NLT 75% |
| | 60 min | 105.06 | 100.52 | 99.07 | — |

In another embodiment, the resulting multiparticulate formulation of the invention achieves a mean AUC of 5451 to 5629 ng.h/ml and mean Cmax of 1865 to 1929 ng/ml or an in-vitro dissolution profile as shown below:

| Batch | % Drug Release* | | | |
|---|---|---|---|---|
| | Acid | Buffer (min) | | |
| | 2 hrs | 15 | 30 | 45 |
| Initial | 0.08 | 101.77 | 107.44 | 107.38 |
| 6 Months @40 C./75% RH | 0.73 | 95.44 | 101.12 | 101.21 |
| 12 Months @25 C./60% RH | 0.30 | 96.11 | 101.92 | 102.20 |

*Specifications: Acid at 2 hrs-NMT 10.0%; Buffer at 45 min-NLT 75%

However, the invention is not limited to these exemplary profiles.

Without wishing to be bound by theory, it is believed that final seal coat layer of hydroxypropyl methylcellulose provides a physical barrier for reduced contact between the mucoadhesive Eudragit layer and the upper GI tract, and thereby allows the reliable transit of the multiparticulates to the proper pH environment in the GI tract for effective release and absorption of the drug. In addition, the final seal coat layer of hydroxypropyl methylcellulose imparts anti-sticking properties to the multiparticulates and thus the multiparticulates are not sticking to the pouch material and/or nasogastric tube. The multiparticulates of the invention are useful for administration via the nasogastric tube and via food vehicles, particularly acidic food vehicles.

II. Method of Producing Multiparticulate Formulations of Invention

In another aspect, the invention provides a method of producing the multiparticulate formulations of the invention.

Typically, the uncoated pantoprazole compounds are prepared are follows. The dry components, including, at least the pantoprazole compound and the binder are dry blended in a suitable mixer under low shear conditions. Suitable low shear conditions can be readily achieved using, e.g., a Hobart mixer, at a range of about 25 rpm to 35 rpm, and most desirably, 32 rpm. However, one of skill in the art will be able to achieve comparable low shear conditions using different equipment, with the rpm adjusted to the appropriate low shear settings for the selected equipment. Optionally, hydroxypropyl methylcellulose or crospovidone may be substituted or additionally included in this step. Additionally, a pH adjuster may be included in this step.

Subsequently, the liquid components, e.g., the surfactant and water, are mixed in to afford a granulated product by mixing under low shear conditions. Suitable low shear conditions can be readily achieved using, e.g., a Hobart mixer, at a range of about 25 rpm to 35 rpm, and most desirably, 32 rpm. However, one of skill in the art will be able to achieve comparable low shear conditions using different equipment, with the rpm adjusted to the appropriate low shear settings for the selected equipment. The granulation is then extruded and spheronized through a suitable device (e.g., a NICA extruder/spheronizer) and the resulting spheroids are dried, sifted, and optionally blended prior to storage.

The inventors have found that a significant advantage is provided to the stability of the compound when the multiparticulates of the invention are dried at low temperature. Desirably, the spheroid cores of the pantoprazole multiparticulates of the invention are dried to a percent (%) loss-on-drying (LOD) of 3.4% to 4.3%. As used herein, low temperature drying refers to a temperature not exceeding about 40° C. for a period of 10 to 12 hours. When the drying conditions exceed this temperature and time period, impurities are observed that contribute to instability. In one embodiment, drying of the core is performed in the range of 35° C. to 40° C., or about 37° C. to 39° C. for about 8 to 72 hours. In another embodiment, the core is dryed at about 40° C. for 10 to 12 hours. Suitably, when coating layers are applied as described, the drying temperature for the various coating layers is also in this range.

Optionally, an initial seal coat of a hydrophilic polymer can be applied to the uncoated multiparticulates. For example, an initial seal coat composed of hydroxypropyl methylcellulose and purified water can be applied on a fluid bed coater, e.g., by spraying.

The enteric coat can be applied directly to the uncoated spheroid core, i.e., the uncoated multiparticulate, or may be applied over an initial seal coat. The enteric coat as described above, is typically applied on a fluid bed wurster coater.

In one embodiment, a final seal coat is applied over the enteric coat and, optionally, talc is utilized in the final step prior to filling the multiparticulates into a suitable packaging unit.

The multiparticulate of the invention may be in any suitable form including, e.g., granules, pellets, beads, minitabs, spherules, beadlets, microcapsules, millispheres, nonocapsules, microspheres, platelets, tablets, and capsules, depending upon the desired route of delivery.

III. Formulations, Kits and Methods of Delivery

In another embodiment, the present invention provides products containing the pantoprazole multiparticulates of the invention.

Suitably, the multiparticulate compositions of the invention are formulated such that a patient receives a suitable amount of the pantoprazole, e.g., 5 mg to 200 mg, about 10 mg to about 100 mg, or about 40 mg (measured based upon free pantoprazole). Preferably, the formulations are such that a suitable dose is delivered in a single dosage unit. These doses may be administered daily for a suitable period of time, e.g., 4 weeks to 8 weeks, but can be delivered for a shorter period of time, e.g., 3 days to 3 weeks, one week to 3 months, or over a longer period, e.g., over 6 months, or longer. These compositions can be delivered alone or in combination with an antacid or other suitable composition.

In one embodiment, the invention provides a method of treating humans by administering an effective dose of the pantoprazole multiparticulates such that an area under curve (AUC) at least bioequivalent to Protonix® 40 mg tablet and Cmax as listed in Table VI are achieved.

In one embodiment, the pantoprazole multiparticulates are packaged for use by the patient or his caregiver. For example, the multiparticulates can be packaged in a foil or other suitable package and is suitable for mixing into a food product (e.g., applesauce and other acidic food vehicles) or into a drink for consumption by the patient.

The pantoprazole multiparticulate formulations of the invention are useful for treatment of gastroesophageal reflux disease (GERD), ulcers of the stomach and duodenum, and Zollinger-Ellison Syndrome.

In another embodiment, the pantoprazole multiparticulates are suspended in a physiologically compatible suspending liquid.

In yet another embodiment, the pantoprazole multiparticulates are filled in capsules, caplets or the like for oral delivery.

In still a further embodiment, the invention provides method of treating a subject in need thereof by administering an effective dose of the pantoprazole multiparticles of the invention.

The following examples illustrate specific embodiments of the invention and are not a limitation on the present invention.

EXAMPLE 1

Pantoprazole Sodium Multiparticulate Formulations

Using a NICA extruder/spheronizer, during initial formulation development, several prototypes of uncoated multiparticulates were manufactured to obtain a target immediate release profile similar to or faster than the pantoprazole sodium uncoated tablet, currently available as Protonix (20 mg and 40 mg) tablets. Levels of the disintegrant crospovidone from 5 to 28.5% and the binder hydroxypropyl methyl cellulose from 0.5 to 1% were evaluated during preparation of uncoated multiparticulates over four batches.

A. Preparation of Uncoated Pantoprazole Sodium Multiparticulates

More particularly, pantoprazole sodium sesquihydrate, microcrystalline cellulose, hydroxypropyl methylcellulose (hypromellose 2208), crospovidone and sodium carbonate are dry blended in a Hobart mixer. Thereafter, polysorbate 80, NF (vegetable source) and purified water, USP, are added to the Hobart mixer. The resulting granulated produce is extruded and spheronized in a NICA® extruder/spheronizer and the spheroids are tray dried at a temperature not beyond 40° C. and sifted, followed by transfer to a PK blender. The final spheroids are stored in drums.

One of the batches (an approximately 200 gm batch) with 15% disintegrant crospovidone and with 1% hydroxypropyl methylcellulose (Hypromellose 2208)-was selected as a prototype with similar release profile. The sieve cut of the uncoated spheroids from this batch was between 500-1000 microns.

B. Prototype Lab Batch (Batch A)

Approximately 100 grams of these uncoated spheroids were coated in a 3" Wurster Fluid Bed coater with Eudragit L30D-55 and hypromellose to result in Enteric coated multiparticulates.

During coating for this batch, the level of hydroxypropyl methyl cellulose (HPMC) initial seal coat was 4% of the weight of the uncoated multiparticulates. The % w/w of the dry polymer Eudragit L30D-55 used was 22.16%. In the coating batch, talc was introduced as dry powder in the coating chamber instead of being a part of the suspension. This was due to the small nozzle size (0.5 mm) used for coating the 100 g batch, which could potentially be clogged. The percent of talc and triethyl citrate used for the lab batch was less as compared to the clinical batches which were subsequently prepared. The multiparticulates were hand filled into size #2 HPMC capsules at a fill weight of 206 mg. The capsules were tested in vitro in 0.11 N HCl and pH 6.8 phosphate buffer. Less than 1% was released in acid media in 2 hours and greater than 80% was released in basic media in 45 minutes as desired.

These capsules were tested in dogs. The $C_{max}$ and AUC were 110 compared against the current marketed Protonix 20 mg tablet (and values were extrapolated to the 40 mg strength). It was seen that these multiparticulates released drug at a much faster rate than the current Protonix tablet in pH 6.8 phosphate buffer as desired. The final seal coat comprises hydroxypropyl methylcellulose (hypromellose) and water. This batch was packaged as spheroids in clear glass vials and placed on stability at accelerated conditions (30° C./65% relative humidity (RH) and 40° C./75% RH). The stability was monitored for 3 months. The potency and dissolution results are presented in Table I. The multiparticulates were stable over the three month period and a 40 mg equivalent dose of multiparticulates filled into capsules at each stability time point met all dissolution and stability criteria.

Dissolution was tested by filling the stored spheroids into capsule shells, and dissolving in 0.1 N HCl (target release at 2 hours: not more than (NMT) 10%), followed by dissolution in pH 6.8 phosphate buffer (target release at 45 min: not less than (NLT) 75%. The acceptance criteria further required a strength of 90 to 110% of the label claim.

TABLE I

Stability of multiparticulates in clear glass vials.

| Test Unit | Time | Strength (HPLC) % Label | Dissolution-Percentage Released (avg) | |
|---|---|---|---|---|
| | | | 0.1 N HCl | Secondary dissolution in phosphate buffer |
| Initial | | 100.0% | 0.9% | 91.6% |
| Ambient Room Temp | 1 month | 97.2% | 0.8% | 88.5% |
| | 7 month | 108.5% | 0.8% | 94.1% |
| 30° C./60% RH | 1 month | 99.3% | 0.5% | 83.4% |
| | 2 month | 98.3% | NA | NA |
| | 3 month | 104.4% | 0.7% | 82.2% |
| 40° C./75% RH | 1 month | 95.4% | 0.7% | 86.1[1] |
| | 2 month | 97.3% | NA | NA |
| | 3 month | 102.7% | 0.7% | 89.4% |

[1] One capsule-78% released.

EXAMPLE 2

Coated Pantoprazole Sodium Multiparticulate Formulations (Batch B)

Based upon the lab batch A, a further scale-up batch of 1400 g was manufactured using a 7" wurster fluid bed coater. During coating for this batch, the level of hydroxypropyl methyl cellulose initial seal coat was 2% of the weight of the uncoated multiparticulates as compared to 4% for the coated Batch A. The % w/w of the dry polymer, Eudragit L30D-55 used was 22.16% w/w. Also, the talc was added directly to the coating suspension as a larger nozzle size (1 mm) was used.

Initial release of coated multiparticulates in 0.1 N acid was high (9.0%) and very close to the limit of 10%. This Batch (B) did not meet the stability and dissolution criteria when tested at accelerated conditions (30° C./60% relative humidity (RH) and 40° C./75% RH). Trial from this batch indicated that an initial seal coat of greater than 2% of uncoated multiparticulates enhances stability of the multiparticulates. Additionally, more enteric polymer loading may be beneficial to control the release in acid media as the process is scaled up.

EXAMPLE 3

Preparation of Pantoprazole Multiparticulates Scale-Up Batch

A. Technical Batch

Using a NICA extruder/spheronizer, a 36 kg technical batch of uncoated multiparticulates was prepared and 20 kg of this batch were enteric coated in a Glatt GPCG-15 machine to result in a 32 kg batch of coated multiparticulates. The % w/w of the dry polymer, Eudragit L30D-55 used was 22.16% w/w. This batch was filled into size #3 HPMC capsules at a fill weight of 156 mg. The release in 0.1 N HCl at 2 hours was greater than the desired 10%. Based on this, taking into account scale-up effects, minor adjustments were made to the formula and process for clinical batch.

B. Clinical Batch

Two 12 kg sub batches of a wet granulated mass were extruded and spheronized on a NICA extruder/spheronizer resulting in wet multiparticulates. The multiparticulates were tray dried at 40° C. for 10 to 12 hours to the desired % LOD of 3.4% to 4.3%. The batch was screened and only 16 kg of uncoated multiparticulates were used for coating to ensure uniformity and completeness of coating in the GPCG-15 machine. The sieved uncoated multiparticulates were coated with an initial hydroxypropyl methycellulose seal coat, followed by an Eudragit L30D-55 enteric coat, followed by a hydroxypropyl methycellulose final coat to result in 33 kg of coated multiparticulates. This batch was filled into size #2 HPMC capsules at a fill weight of 206 mg.

The release in 0.1 N HCl at 2 hours was less than the 10% limit and in pH 6.8 phosphate buffer, it was greater than the 80% limit at 45 minutes. The batch met in vitro release characteristics. The one month stability date showed that the multiparticulates were stable at 40° C./75% RH for one month. Currently, this batch is stable up to one year at room temperature and up to 6 months at 40 deg.C/75% RH. Stability study at room temperature condition beyond one year is ongoing. The one year room temperature stability results of this batch are shown in the following Table II.

The spheroid filled capsule had a faster in vitro release (dissolution) as compared to the Protonix 40 mg tablet in pH 6.8 phosphate buffer.

TABLE II

Stability of Pantoprazole Sodium Spheroid-filled Capsules, 40 mg

| Test | Appearance and Description | Strength (HPLC) | Water (KF) | Purity | | Dissolution | |
|---|---|---|---|---|---|---|---|
| Specification | #2 Opaque white capsules (cap and body) containing white to off-white colored spheroids | 90.0–110.0% Label Claim (LC) | For Information | Largest Single Known or Unknown Impurity ≦0.5 (RRT) | Total Known and Unknown Impurities ≦2.0 | Dissolution in 0.1 N HCl NMT 10% in 2 hrs. Conforms to USP <724> | Dissolution in Phosphate Buffer NLT 75% in 45 min. Conforms to USP <724> |
| Unit | | % | % | % | % | % | % |
| Initial | Conforms | 100.3 | 5.1 | BRL | BRL | 0 | 105 |
| Initial | | | | | | 0 | 107 |

TABLE II-continued

Stability of Pantoprazole Sodium Spheroid-filled Capsules, 40 mg

| Test | Appearance and Description | Strength (HPLC) | Water (KF) | Purity | | Dissolution | |
|---|---|---|---|---|---|---|---|
| (Spheroids only)[a] 25° C./60% RH | | | | | | | |
| 1 Month | No Change | 99.5 | 5.2 | 0.17 (1.39) | 0.17 | 1 | 103 |
| 2 Month | No Change | 101.4 | 4.6 | 0.15 (1.38)[b] | 0.23 | 0 | 101 |
| 3 Month | No Change | 101.2 | 4.5 | 0.17 (1.39) | 0.17 | 0 | 100 |
| 6 Month | No Change | 101.3 | 4.5 | 0.18 (1.38)[b] | 0.24 | 0 | 100 |
| 6 Month (Spheroids only)[a] | | | | | | 0 | 112 |
| 9 Months | No Change | 99.2 | 5.1 | 0.21 (1.40)[b] | 0.33 | 0 | 101 |
| 9 Months (Spheroids only)[a] | | | | | | 0 | 108 |
| 12 Months | No Change | 99.1 | 5.1 | 0.08 (0.14) | 0.23 | 0 | 102 |
| 12 Months (Spheroids only)[a] | | | | | | 0 | 104 |

BRL = Below Reporting Limit (0.05%).
NMT = Not more than.
NLT = Not less than.
RRT = Relative retention time.
[a]Initial and revalidation dissolution results are provided for Pantoprazole Sodium Spheroids, 40 mg/206 mg, which is the ingoing batch of spheroids used for manufacture of Pantoprazole Sodium Spheroid-filled Capsules, 40 mg.
[b]Corresponds to the impurity at RRT = 1.39.

EXAMPLE 4
Evaluation of Batch A Formulation in Beagle Dogs

The in-vitro release data of the sodium pantoprazole multi particulate formulation shows a faster release than the current marketed tablet. This provides earlier absorption and thereby a faster onset of action. The dog data clearly shows earlier drug levels of sodium pantoprazole from multiparticulates as compared to the single monolithic tablets. Earlier onset of action provides faster relief from gastric pain and other gastrointestinal (GI) disorders.

Pantoprazole sodium formulations have been evaluated in Beagle Dogs (n=5). The mean (SD) pharmacokinetic parameters and relative bioavailability of pantoprazole is illustrated in the Table III below.

As illustrated, the non-optimized lab batch of sodium pantoprazole multiparticulate formulation dosed in dogs shows smaller lag time than the current marketed tablet. In the following table, AUC refers to the area under a curve plotting mean concentration against protocol time. $C_{max}$ refers to the maximum observed concentration value in the blood sample after administration. $T_{max}$ refers to the time point when C max occurs. $T_{lag}$ refers to the time following administration before effective amounts of the drug are observed in the circulation; $t_{1/2}$ (hr) provides the half-life for drug elimination. Relative bioavailability compares the absorption of a product from the gut in comparison with a dose given intravenously (assumed 100%).

TABLE III

The mean (SD) pharmacokinetic parameters and relative bioavailability of pantoprazole

| Parameter | 20 mg Market Tablet Batch A Pantoprazole Na[a] | 40 mg Multiparticulate Capsule Batch A with enteric coat - Pantoprazole Na |
|---|---|---|
| AUC (μg*hr/mL) | 16.3 (2.46) | 17.3 (2.33) |
| Cmax (μg/mL) | 11.7 (3.55) | 7.10 (1.76) |
| Tmax (hr) | 1.70 (0.84) | 1.20 (0.27) |
| tlag (hr) | 1.10 (0.91) | 0.25 (0.18) |
| t ½ (hr) | 0.62 (0.17) | 0.77 (0.21) |
| Relative Bioavailability | — | AUC: 106%[b] Cmax: 61%[b] |

[a]AUC and Cmax are normalized to a 40 mg dose
[b]Relative to Market Product Tablet The dog data of the sodium pantoprazole multi particulate formulation gives a similar AUC as the current marketed tablet. Without wishing to be bound by theory, it is believed that the faster release and similar AUC of the multi particulates is achieved by lowering the level of the disintegrating agent crospovidone (as compared to the level in the tablet) and incorporating the functional excipient polysorbate 80 in the core of the spheroids.

EXAMPLE 5
Pantoprazole Sodium Sesquihydrate:Excipient Formulations

This study was performed to determine the compatibility of pantoprazole sodium sesquihydrate with hypromellose 2208, sodium lauryl sulfate (SLS), crospovidone, and polysorbate-80.

A. Study Design

The study consists of two sets of samples. The first set contained drug and excipient. The second set contained drug, excipient and approximately 2 μl water. The reason for the water along with the drug and the excipient is to see whether additional water present causes any incompatibility.

The excipients were mixed with the drug in the ratio indicated in the following table. The excipients and the drug were weighed into a glass vial. Then the vials were vortexed for 15 seconds. Similarly, a second set of samples was prepared. Approximately 2 μl (the smallest amount of water that can be added with the pipette in the lab) was added to these vials.

Then the vials were vortexed for 5 seconds. Finally, the first and second set of vials were capped and placed in stability chambers. The conditions tested were 40°/75% RH and 51° C. for 3 weeks.

B. Results

The results of this drug-excipient compatibility study are presented as % recovery in the Table IV below. The selection criteria for the compatibility or in-compatibility are based on the % recovery between 90-110%.

TABLE IV

Drug: Excipient Compatibility Results

| | | % Recovery | | | |
|---|---|---|---|---|---|
| | | Drug + Excipient | | Drug + Excipient + Water | |
| Excipient | Ratio of Drug:Excipient | 40° C./75% RH 3 weeks | 51° C. 3 weeks | 40° C./75% RH 3 weeks | 51° C. 3 weeks |
| Control (Drug alone) | — | 94.67 | 100.53 | 94.60 | 96.64 |
| Hypromellose 2208, USP, 3 cps | 10:1 | 99.209 | 93.248 | 93.811 | 97.421 |
| Sodium Lauryl Sulfate (SLS) | 5:3 | 99.947 | 98.763 | 95.466 | 95.088 |
| Crospovidone, NF | 10:1 | 100.080 | 98.908 | 97.201 | 105.716 |
| Polysorbate-80, NF BP/EP (vegetable source) | 10:1 | 98.301 | 90.961 | 99.908 | 81.405 |

From the results shown in the table, the following conclusions can be drawn. Hypermellose 2208, SLS, crospovidone and polysorbate-80 are compatible with pantoprazole sodium sequihydrate at 40° C./75% RH for 3 weeks. Hypromellose 2208, SLS and crospovidone are compatible with pantoprazole sodium sequihydrate at 40° C./75% RH and 51° C. with and without additional water for 3 weeks.

In this study degradation compounds were not studied. However, the pediatric clinical formulation, [pantoprazole sodium sesquihydrate 45.24% w/w; microcrystalline cellulose 27.25% w/w; polysorbate 80 5% w/w; crospovidone 15% w/w; hypromellose 2208 1% w/w; sodium carbonate 6.5% w/w; purified water q.s.], was studied under accelerated conditions of 40° C./75% RH and is stable up to 6 months, providing a 2 year room temperature shelf life.

The components of the pediatric formulation are provided in the following Table V.

| | Multiparticulates | |
|---|---|---|
| Formulation: Ingredients | Amount/ Capsule | % w/w |
| Core: | | |
| Pantoprazole Sodium Sesquihydrate | 45.11 | 21.911 |
| Microcrystalline Cellulose, NF/EP (Avicel PH 101) | 27.39 | 13.304 |
| Polysorbate 80, NF Vegetable source | 5.00 | 2.429 |
| Crospovidone, NF (Polyplasdone XL) | 15.00 | 7.286 |
| HPMC USP/EP (Methocel) K3 | 1.00 | 0.486 |
| Sodium Carbonate, NF | 6.50 | 3.157 |
| Purified Water, USP/BP/EP | | q.s. to make wet mass* |
| Total | 100.00 mg | 48.573 |
| Enteric Coat: | 100.20 mg | 48.67 |
| Eudragit L30D-55 | 208.00 mg 62.40 (solids) | 30.309 |
| Talc, USP, Altalc 500V | 31.20 mg | 15.155 |
| Sodium Hydroxide, NF 1 N solution | 9.30 mg 0.36 (solids) | 0.175 |
| Triethyl Citrate, PG/NF | 6.24 mg | 3.031 |
| Purified Water, USP/BP/EP | 183.38 mg* | |
| Total | 204.20 mg | 99.186 |
| Final Seal Coat: | 1.54 mg | 0.748 |
| Hydroxypropyl Methylcellulose, USP 2910, 6 cps | 1.54 mg | 0.748 |
| Purified water, USP/BP/EP | 18.99 mg* | |
| Total | 205.74 mg | 99.934 |
| Talc, USP, Altalc 500V | 0.14 mg | 0.068 |
| Total | 205.88 mg | 100.002 |

*removed during processing

EXAMPLE 6

Evaluation of Pantoprazole Sodium Formulation in Human Adult Subjects

In this study, 40 mg pantoprazole sodium, formulated as described, clinical pediatric formulation, was administered to healthy human adults (n=24) by sprinkling in applesauce, in tablet form, or as an aqueous suspension prepared using an inactive powder blend and water (8 in each group).

In the following Table VI, column 1 provides the pharmacokinetic (PK) parameters, AUC (area under the concentration curve), $AUC_T$ is the area under the concentration time curve, and $C_{max}$, maximum concentration. The second column provides the test/reference geometric mean (GM) ratio. The third column provides the confidence interval for the GM ratio. [The FDA considers a test product to be bioequivalent to a reference product if the 90% confidence interval (CI) of the geometric mean ratio of AUC and $C_{max}$ between the test and reference fall within 80-125%].—The confidence interval is calculated using WinNonlin software.

TABLE VI

Human PK study Results

| PK parameter | Test/Reference GM ratio | 90% CI for ratio* |
|---|---|---|
| A. Spheroids sprinkled in applesauce: | | |
| AUC | 90 | 84-96 |
| $AUC_T$ | 89 | 84-95 |
| Cmax | 62 | 56-70 |
| B. Spheroids in suspension: | | |
| AUC | 94 | 88-100 |
| $AUC_T$ | 94 | 88-100 |
| Cmax | 66 | 60-74 |

The lag time in the absorption of the tablet was higher compared to the sprinkle and suspension formulations. The entire drug in the tablet is released over a small time interval and therefore a higher $C_{max}$ is obtained. With the spheroid formulations, drug from each spheroid is released over a longer time interval and therefore the $C_{max}$ is lower than the tablet. However, the period of time following administration that pantoprazole remained in the circulation is similar for the 3 formulations.

All documents identified herein are incorporated by reference. One of skill in the art will recognize that minor modifications to the conditions and techniques described in the specific embodiments described herein can be varied without departing from the present invention. Such minor modification and variants are within the scope of the invention as defined by the following claims.

The invention claimed is:

1. A method of producing a multiparticulate formulation of pantoprazole having reduced release under gastric conditions and fast release at neutral pH, said method comprising the steps of:
producing a spheroid core comprising about 45% w/w pantoprazole sodium sesquihydrate, as a sole active component in the multiparticulate formulation and about 25% to 30% w/w microcrystalline cellulose, about 4% to 6% w/w polysorbate 80, about 14% to 16% w/w crospovidone, about 0.5 to 2% w/w hydroxypropyl methylcellulose, and about 5% to 8% w/w sodium carbonate a surfactant via extrusion and spheronization, said core further containing about 1 to about 2% w/w water;
applying an initial seal coat comprising hydroxypropyl methylcellulose to the spheroid core,
applying an enteric coating to the initial seal coated spheroid core, said enteric coating comprising a copolymer of methacrylic acid and methacrylates;
and optionally applying a final seal coat to the enteric-coated spheroid core, said final seal coat being about 1 wt % of the multiparticulate;
wherein the multiparticulates have an average diameter of about 0.7 mm to about 1.25 mm.

2. The method according to claim 1, wherein the spheroid core is prepared by mixing the ingredients in a low shear mixer at low shear conditions at a range of about 25 rpm to 35 rpm.

3. The method according to claim 2, wherein the low shear conditions are 32 rpm.

4. The method according to claim 2, wherein the spheroid cores are dried at a low temperature not exceeding about 40° C. for a period of 8 to 72 hours to a percent (%) loss-on-drying (LOD) of 3.4% to 4.3%.

5. The method according to claim 1, further comprising the step of applying a layer of talc in an amount of 0.05% w/w to 0.1% w/w of the multiparticulates.

6. The method according to claim 1, wherein the enteric coating is sprayed as a suspension onto the spheroid core.

7. Pantoprazole multiparticulates having reduced release under gastric conditions and fast release at neutral pH, wherein each of said multiparticulates comprises: a spheroid core comprising about 45% w/w pantoprazole sodium sesquihydrate as a sole active component in the multiparticulates about 25% to 30% w/w microcrystalline cellulose, about 4% to 6% w/w polysorbate 80, about 14% to 16% w/w crospovidone, about 0.5 to 2% w/w hydroxypropyl methylcellulose, about 5% to 8% w/w sodium carbonate, and about 1 to 2% w/w water; an initial seal coat comprising hydroxypropyl methylcellulose on the spheroid core; and an enteric coat on the initial seal coat, wherein said multiparticulates have an average diameter of about 0.7 mm to about 1.25 mm.

8. The multiparticulates according to claim 7, wherein said multiparticulates have an average diameter of about 1 mm.

9. The multiparticulates according to claim 7, wherein said enteric coat comprises about 48% w/w of the particulate, 10. The multiparticulates according to claim 7, further comprising a final seal coat on the enteric coat.

11. The multiparticulates according to claim 10, wherein the final seal coat comprises about 0.1 to 10 wt % of the multiparticulates.

12. The multiparticulates according to claim 10, wherein the final seal coat comprises hydroxypropyl methylcellulose (hypromellose).

13. The multiparticulates according to claim 7 wherein said initial seal coat is in the range of about 2 to about 4% w/w of the weight of the uncoated core.

14. The multiparticulates according to claim 7, wherein the enteric coating comprises about 30% w/w of methacrylic acid and methyacrylate copolymer, about 15% w/w talc, about 3% triethyl citrate and a pH adjuster; said amounts being by weight of the multiparticulates.

15. A pantoprazole formulation comprising a suspension comprising the multiparticulates of claim 7 and a physiologically compatible suspending liquid.

16. A capsule comprising the multiparticulates of claim 7.

17. A foil packet comprising the multiparticulates according to claim 7.

18. The method according to claim 1, wherein the spheroid core consists essentially of:

| | |
|---|---|
| pantoprazole sodium sesquihydrate | about 45% w/w |
| microcrystalline cellulose | about 27% w/w |
| polysorbate 80 | about 5% w/w |
| crospovidone | about 15% w/w |
| hydroxypropylmethylcellulose | about 1% w/w |
| sodium carbonate | about 6.5% w/w: and |
| water. | |

19. The pantoprazole multiparticulates according to claim 7, wherein the spheroid core consists essentially of:

| | |
|---|---|
| pantoprazole sodium sesquihydrate | about 45% w/w |
| microcrystalline cellulose | about 27% w/w |
| polysorbate 80 | about 5% w/w |
| crospovidone | about 15% w/w |
| hydroxypropylmethylcellulose | about 1% w/w |
| sodium carbonate | about 6.5% w/w: and |
| water. | |

20. A plurality of pantoprazole multiparticulates, each comprising: a spheroid core consisting essentially of about 45% w/w pantoprazole sodium sesquihydrate, about 27% w/w microcrystalline cellulose, about 5% w/w polysorbate 80; about 15% w/w crospovidone; about 1% w/w hydroxypropy methylcellulose, about 6.5% w/w sodium carbonate; and water; an inner seal coat comprising hydroxypropyl methylcellulose; and an enteric coating comprising a methacrylic acid and meth[yl]acrylate polymer, and triethylcitrate, wherein multiparticulates have an average diameter in the range of about 0.7 mm to about 1.25 mm.

21. The product according to claim 20, wherein the enteric coating further comprises talc.

22. The product according to claim 21, wherein the enteric coating further comprises sodium hydroxide.

* * * * *

UNITED STATES PATENT AND TRADEMARK OFFICE
CERTIFICATE OF CORRECTION

PATENT NO. : 7,544,370 B2
APPLICATION NO. : 10/955567
DATED : June 9, 2009
INVENTOR(S) : Sripriya Rao et al.

It is certified that error appears in the above-identified patent and that said Letters Patent is hereby corrected as shown below:

Title Page, Item [75] Inventors: Hanumantharao Tatapudy, Suffern, NJ, replace with -- Hanumantharao Tatapudy, Suffern, NY --;

Signed and Sealed this

First Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,544,370 B2 | Page 1 of 1 |
| APPLICATION NO. | : 10/955567 | |
| DATED | : June 9, 2009 | |
| INVENTOR(S) | : Rao et al. | |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (495) days Delete the phrase "by 495 days" and insert -- by 615 days --

Signed and Sealed this

Nineteenth Day of January, 2010

David J. Kappos
*Director of the United States Patent and Trademark Office*